US011006830B2

(12) United States Patent
Sommerlade et al.

(10) Patent No.: US 11,006,830 B2
(45) Date of Patent: May 18, 2021

(54) METHOD AND SYSTEM FOR DETERMINING NETWORK CONNECTIONS

(71) Applicant: GENTING TAURX DIAGNOSTIC CENTRE SDN BHD, Kuala Lumpur (MY)

(72) Inventors: Linda Sommerlade, Aberdeen (GB); Björn Olaf Schelter, Aberdeen (GB); Claude Michel Wischik, Aberdeen (GB)

(73) Assignee: Genting TauRx Diagnostic Centre SDN BHD, Kuala Lumpur (MY)

( * ) Notice: Subject to any disclaimer, the term of this patent is extended or adjusted under 35 U.S.C. 154(b) by 239 days.

(21) Appl. No.: 16/068,468

(22) PCT Filed: Jan. 6, 2017

(86) PCT No.: PCT/EP2017/050269
§ 371 (c)(1),
(2) Date: Jul. 6, 2018

(87) PCT Pub. No.: WO2017/118733
PCT Pub. Date: Jul. 13, 2017

(65) Prior Publication Data

US 2019/0021594 A1 Jan. 24, 2019

(30) Foreign Application Priority Data

Jan. 8, 2016 (MY) ............................ PI2016000032

(51) Int. Cl.
*A61B 5/00* (2006.01)
*A61B 5/369* (2021.01)
*G06F 17/18* (2006.01)

(52) U.S. Cl.
CPC .......... *A61B 5/0006* (2013.01); *A61B 5/0024* (2013.01); *A61B 5/369* (2021.01);
(Continued)

(58) Field of Classification Search
CPC ... A61B 5/0006; A61B 5/0024; A61B 5/0476; A61B 5/7207; A61B 5/7203; A61B 2562/046; G06F 17/18
(Continued)

(56) References Cited

U.S. PATENT DOCUMENTS 9,107,595 B1 * 8/2015 Smyth ................ A61B 5/04012
2013/0123607 A1 5/2013 Leuthardt et al.

FOREIGN PATENT DOCUMENTS

TW 201438671 A 10/2014
TW 201521676 A 6/2015

OTHER PUBLICATIONS

Bullmore et al., "Brain Graphs: Graphical Models of the Human Brain Connectome," Annual Review of Clinical Psychology, vol. 7, No. 1, Apr. 2011, pp. 113-140.
(Continued)

*Primary Examiner* — David J. McCrosky
*Assistant Examiner* — Chanel J Jhin
(74) *Attorney, Agent, or Firm* — Wolf, Greenfield & Sacks, P.C.

(57) ABSTRACT

This invention relates to methods and systems for determining network connections. It is particularly, but not exclusively, related to methods and systems for determining network connections in sparse networks, and has particular application to EEG data. An aspect of the invention provides a method for identifying, in a network of interacting nodes simultaneously producing signals, connections between said nodes and of estimating connection coefficients between nodes identified as connected which includes the steps of setting to zero connection coefficients where the calculated coherence or partial coherence is below a first predetermined threshold and subsequently setting to zero connection coefficients where the estimated connection coefficients are
(Continued)

below a second predetermined threshold, and then re-estimating the connection coefficients for the combinations of nodes for which the connection coefficients have not already been set to zero.

13 Claims, 14 Drawing Sheets

(52) U.S. Cl.
CPC ............ *A61B 5/7207* (2013.01); *G06F 17/18* (2013.01); *A61B 5/7203* (2013.01); *A61B 2562/046* (2013.01)

(58) Field of Classification Search
USPC .......................................................... 600/544
See application file for complete search history.

(56) References Cited

OTHER PUBLICATIONS

Hesse et al., "The use of time-variant EEG Granger causality for inspecting directed interdependencies of neural assemblies," Journal of Neuroscience Methods, vol. 124, 2003, pp. 27-44.
International Search Report and Written Opinion issued in corresponding application No. PCT/EP2017/050269 dated Apr. 7, 2017.
Jie et al., "Integration of Network Topological and Connectivity Properties for Neuroimaging Classification", IEEE Trans Biomed Eng, vol. 61, No. 2, 2014, pp. 576-589.
Kaminski et al., "A new method of the description of the information flow in the brain structures," Biological cybernetics, vol. 65, 1991, pp. 203-210.
Kaminski et al., "Topographic analysis of coherence and propagation of EEG activity during sleep and wakefulness," Electroencephalography and clinical Neurophysiology, vol. 102, 1997, pp. 216-227.
Keyl et al., "Cardiocirculatory coupling during sinusoidal baroreceptor stimulation and fixed-frequency breathing," Clinical Science, vol. 99, 2000, pp. 113-124.
Korzeniewska et al., "Information flow between hippocampus and related structures during various types of rat's behavior," Journal of Neuroscience Methods, vol. 73, 1997, pp. 49-60.
Lee et al., "Sparse Brain Network Recovery Under Compressed Sensing," IEE Transactions on Medical Imaging, vol. 30, No. 5, 2011, pp. 1154-1165.
Lutkepohl et al., "3.3 Least Squares Estimation with Mean-Adjusted Data and Yule-Walker Estimation," Estimation of Vector Autoregressive Processes, 2005, pp. 82-87.
Nollo et al., "Exploring directionality in spontaneous heart period and systolic pressure variability interactions in humans: implications in the evaluation of baroreflex gain," Am J Physiol Heart Circ Physiol, vol. 288, 2005, pp. H1777-H1785.
Nolte et al., "Robustly Estimating the Flow Direction of Information in Complex Physical Systems," Physical Review Letters, vol. 100, 2008, pp. 234101-1-234101-4.
Palus et al., "Direction of coupling from phases of interacting oscillators: An information-theoretic approach," Phsyical Review E, vol. 67, 2003, pp. 055201-1-055201-4.
Palus et al., "Directionality of coupling from bivariate time series: How to avoid false causalities and missed connections," Physical Review E, vol. 75, 2007, pp. 056211-1-056211-14.
Pitzalis et al., "Effect of respiratory rate on the relationships between RR interval and systolic blood pressure fluctuations: a frequency-dependent phenomenon," Cardiovascular Research, vol. 38, 1998, pp. 332-339.
Pompe et al., "Using Mutual Information to Measure Coupling in the Cardiorespiratory System, IEEE Engineering in Medicine and Biology," 1998, pp. 32-39.
Priestley et al., "9.1 Correlation and Spectral Properties of Multivariate Stationary Processes", Correlation and Spectral Properties, 1981, pp. 655-668.
Prusseit et al., "Measuring interdependences in dissipative dynamical systems with estimated Fokker-Planck coefficients," Physical Review E, vol. 77, 2008, pp. 041914-1-041914-10.
Romano et al., "Estimation of the direction of the coupling by conditional probabilities of recurrence," Physical Review E, vol. 76, 2007, pp. 036211-1-036211-9.
Rosenblum et al., "Detecting direction of coupling in interacting oscillators," Physical Review E, vol. 64, 2001, pp. 045202-1-045202-4.
Rosenblum et al., "Identification of coupling direction: Application to cardiorespiratory interaction," Physical Review E, vol. 65, 2002, pp. 041909-1-041909-11.
Sameshima et al., "Using partial directed coherence to describe neuronal ensemble interactions," Journal of Neuroscience Methods, vol. 94, 1999, pp. 93-103.
Schad et al., "Approaches to the Detection of Direct Directed Interactions in Neuronal Networks," Springer Series in Computational Neuroscience, 2009, pp. 43-64.
Schelter et al., "Assessing the strength of directed influences among neural signals using renormalized partial directed coherence, Journal of Neuroscience Methods," vol. 179, 2009, pp. 121-130.
Schreiber, Thomas, Measuring Information Transfer, Physical Review Letters, vol. 85, No. 2, 2000, pp. 461-464.
Sommerlade et al., "Assessing the strength of directed influences among neural signals: An approach to noisy data," Journal of Neuroscience Methods, vol. 239, pp. 47-64, 2015.
Staniek et al., Symbolic Transfer Entropy, Physical Review Letters, vol. 100, pp. 158101-1-158101-4, 2008.
Strogatz, Steven, "Exploring complex networks," Nature, vol. 410, Mar. 2001, pp. 268-276.
Tass et al., "Detection of n:m Phase Locking from Noisy Data: Application to Magnetoencephalography," Physical Review Letters, vol. 81, No. 15, 1998, pp. 3291-3294.
Ting et al., "A Kalman Filter for Robust Outlier Detection," Proceedings of the 2007 IEEE/RSJ International, 2007, pp. 1514-1519.
Vejmelka et al., "Inferring the directionality of coupling with conditional mutual information," Physical Review E, vol. 77, 2008, pp. 026214-1-026214-12.
Weber et al., "Reproducibility of functional network metrics and network structure: A comparison of task-related BOLD, resting ASL with BOLD contrast, and resting of cerebral blood flow," Cogn Affect Behav Neurosc, vol. 13, No. 3, 2013, pp. 627-640.
Examination Report issued in corresponding European Patent Application No. 17700316.7 dated May 24, 2019.
Makhtar Siti N et al: "Multivariate partial coherence analysis for identification of neuronal connectivity from multiple electrode array recordings", 2014 IEEE Conference on Biomedical Engineering and Sciences (IECBES), IEEE, Dec. 8, 2014 (Dec. 8, 2014), pp. 77-82, XP032739016, DOI: 10.1109/IECBES.2014.7047613.

* cited by examiner

METHOD AND SYSTEM FOR DETERMINING NETWORK CONNECTIONS

CROSS REFERENCE TO RELATED APPLICATIONS

The present application is a national stage entry of International Patent Application No. PCT/EP2017/050269, filed Jan. 6, 2017, which claims priority to Malaysian Patent Application No. PI2016000032, filed Jan. 8, 2016, each of which is incorporated herein by reference in its entirety.

FIELD OF THE INVENTION

The present invention relates to methods and systems for determining network connections. It is particularly, but not exclusively, related to methods and systems for determining network connections in sparse networks, and has particular application to EEG data.

BACKGROUND OF THE INVENTION

Networks of interacting nodes, each with its own dynamics, are a key mathematical tool for the description of complex systems (Strogatz, 2001). Depending on the particular application, the dynamics of the individual nodes, their coupling structure or their collective behaviour all determine the dynamics of the system. In the neurosciences, for instance, detecting interactions between signals, i.e. the coupling structure among nodes, is of particular interest. Understanding brain networks promises to disclose the biological basis underlying natural behaviour or certain diseases (e.g. Hesse et al., 2003; Tass et al., 1998; Pitzalis et al., 1998; Keyl et al., 2000; Nollo et al., 2005; Bowers and Murray, 2004). Several techniques have been proposed so far to infer the network structure of complex systems from observed signals. These include but are not limited to transfer entropy (Schreiber, 2000; Staniek and Lehnertz, 2008), recurrences in state space (Arnhold et al., 1999; Chicharro and Andrzejak, 2009; Romano et al., 2007), mutual information (Pompe et al., 1998; Paluš and Stefanovska, 2003; Paluš and Vejmelka, 2007; Vejmelka and Paluš, 2008; Frenzel and Pompe, 2007), phase dynamics (Rosenblum and Pikovsky, 2001; Rosenblum et al., 2002), coherence (Halliday and Rosenberg, 2000; Dahlhaus, 2000; Nolte et al., 2008), the Fokker Planck formalism (Prusseit and Lehnertz, 2008; Bahraminasab et al., 2009), compressed sensing (Lee et al., 2011), or autoregressive modelling (Dahlhaus and Eichler, 2003; Eichler, 2000; Korzeniewska et al., 1997; Kamiński et al., 1997; Kamiński and Blinowska, 1991; Arnold et al., 1998).

Recent years have seen a large increase in the availability of data. The number of channels that are simultaneously recorded has increased. With respect to network analysis this leads to the challenge of estimating high-dimensional networks. The aim is to estimate only direct connections in the network. Additionally it is desirable to also draw conclusions about the direction of the connections. Approaches to investigate the direction of an influence use the concept of causality. Many methods (e.g. Hesse et al., 2003; Geweke, 1982, 1984; Chen and Wasterlain, 2006; Dhamala et al., 2008; Baccalá and Sameshima, 2001; Sameshima and Baccala, 1999; Eichler, 2006; Kamiński and Blinowska, 1991) are based on Granger's definition of causality (Granger, 1969). Briefly, this definition states that a process x1 is causal for another process x2, if x1 is useful for the prediction of the future of x2. Linear Granger-causality is typically modelled by means of vector autoregressive processes, which are estimated via multivariate Yule-Walker equations or similar approaches (Lütkepohl, 2005). In most large networks the adjacency matrix is sparse. This means that out of all the possible connections only a few are present.

The present inventors have realised how assuming a sparse network can be used to improve parameter estimation of the vector autoregressive process.

Existing commonly used methods which may be used to determine the coupling structure include coherence and partial coherence, which can be estimated as presented in Schad et al. (2009). A further technique is directed partial correlation (Eichler, 2005, 2006). All of these have limitations as set out in more detail below. In particular, existing methods can typically only cope with a maximum of 10 nodes in the potential network before the methods start to significantly lose accuracy and/or become unacceptably long or computationally demanding.

Throughout this document, autoregressive coefficients are estimated according to Lütkepohl (2005), although other methods can be used.

In a first scenario, a 15-dimensional network of coupled white noise processes is analysed. FIG. 1 shows the graph of the simulated network. Using simulated data, the reconstructed graphs for coherence and partial coherence are shown in FIGS. 2(*a*) and 2(*b*), respectively. Both reconstructed graphs show the same number of sub-graphs but apart from that are very different from the original one.

In a second scenario, the six-dimensional autoregressive process of order one $$\vec{x}(t)=A\vec{x}(t-1)+\vec{\varepsilon}(t) \tag{1}$$

is considered, where ε is a multivariate Gaussian white noise process and $$A=\begin{pmatrix}0.8&0&0&0&0&0\\0&0&0&0.4&0&0\\0&0&0&0&-0.5&0\\0.6&0&0&0&0&0\\0&0&0.6&0&0&0\\0&0&0&0&0&0.8\end{pmatrix} \tag{2}$$

M=100 realisations of N=200 data points each were simulated. The simulated network is summarized in the graph in FIG. 3. For the estimation, the true autoregressive process order (p=1) is used.

For all 36 coefficients, the absolute value of the difference between the true and the mean estimated coefficient is shown in FIG. 4. Error bars refer to the standard deviation of the mean for 100 realisations. This result shows that all estimated coefficients are very close to their respective true values even though only 200 data points were used in the simulation.

The system investigated here is a sparse system but since it is rather low-dimensional, ordinary parameter estimation can still handle it.

In a third scenario a much higher dimensional system is used. This is a 40-dimensional network of coupled white noise processes. Connections are present either at lag 1 or at lag 2. The graph of the simulated network is shown in FIG. 5. N=10,000 data points of this system were simulated. The estimated networks, based on coherence and partial coherence, are shown in FIGS. 6(*a*) and (*b*) respectively. Neither of them yields a meaningful representation of the underlying network.

For directed partial correlation analysis (Eichler, 2005, 2006), the true process order p=2 is used. The resulting estimated network is shown in FIG. 7.

Some additional connections show up in this analysis (shown by dashed arrows in FIG. 7). These are false positive conclusions. They occur because of the great number of coefficients that need to be estimated in this high-dimensional network.

Electroencephalography ("EEG") provides multi-channel data of brain activity from a plurality (usually at least 20) small sensors attached to the scalp of an individual which detect the voltage fluctuations resulting from ionic current flows within the neurons of the brain when brain cells send messages to each other. Due to the plurality of sensors, the data from EEG has a corresponding plurality of channels. EEG is currently used to help diagnose and monitor a number of conditions affecting the brain, particularly epilepsy.

For some time, EEG has been employed clinically as a measure of brain function in the hope of determining and differentiating certain functional conditions of the brain. However, to date, progress has been slow.

The present inventors have realised that the possibility of accurately determining networks of causal relationships within EEG data may allow further interpretation of this data for clinical purposes.

EEG data is multi-dimensional and so susceptible to analysis in a network fashion. Many types of EEG data now have a large number of channels (e.g. 20 or more). Traditional methods of analysis can struggle to provide meaningful information or interpretation of such multi-variate data and so new approaches are required to handle the multi-order systems which are being observed.

In particular in the diagnosis and treatment of Alzheimer's disease, it is now being recognised that Alzheimer's disease is a long time (possibly of the order of 20 years) in development before frank symptoms are observed. Accordingly, there is considerable focus on techniques which may provide for reliable early-stage identification of potential suffers or of those exhibiting particular susceptibility or risk factors. These techniques aim to identify the onset of early-stage Alzheimer's disease in the entirely pre-clinical stage (typically 10-20 years before onset) or in the prodromal period.

The use of EEG data to identify early symptoms or warning signs of Alzheimer's disease has particular attractions if suitable methods exist for the robust analysis of the data as it is a standard and widely-used and available technique. It is also available, in certain implementations, in a form which can be effectively self-applied by an individual with little or no training and so is eminently suitable for the primary care setting.

The present invention aims to provide methods and systems which provide accurate and reliable predictions of network connections and coefficients, particularly in sparse networks.

A further aim of the present invention is to provide efficient methods for predicting network connections and coefficients.

A further aim of the present invention is to provide methods and systems for processing EEG data to provide meaningful information and/or interpretation of the data through network overviews of brain activity and to permit subsequent uses of such data.

SUMMARY OF THE INVENTION

At their broadest, aspects of the present invention provide methods and systems for identifying connections between nodes in a network which operate by identifying probable zero connection coefficients and setting them to zero for subsequent processing.

A first aspect of the present invention provides a method of identifying, in a network of interacting nodes simultaneously producing signals, connections between said nodes and of estimating connection coefficients between nodes identified as connected, the method including the steps of: periodically recording the signal at each node over a predetermined period of time to form a data set; calculating the coherence and partial coherence between each combination of nodes in the data set; checking, for each combination of nodes, if either the coherence or the partial coherence is below a first predetermined threshold and, if so, setting the corresponding connection coefficient to zero for all subsequent steps; a first estimating step of estimating, from the data set, the connection coefficients for the combinations of nodes for which the connection coefficient has not already been set to zero; for each connection coefficient estimated by said first estimating step to be below a second threshold, setting said coefficient to zero for all subsequent steps; and a second estimating step of re-estimating, from the data set, the connection coefficients for the combinations of nodes for which the connection coefficients have not already been set to zero.

The method of this aspect contains two "zeroing" steps prior to the final step of estimating the connection coefficients. These act to remove indirect links (by consideration of partial coherence and coherence). This can reduce or eliminate false positives from the determined network.

The method of this aspect just uses data. It does not rely on any predictions or assumptions about the underlying model.

The method of this aspect assumes a degree of sparseness in the network, implying that some of the coefficients in the adjacency matrix are zero. Based on this assumption the estimation procedure is improved by identifying coefficients which are candidates for zeroing and setting these to zero before performing further calculations or estimations. The method of this aspect is therefore also more efficient at predicting connections in a sparse network than existing methods. Accordingly the method is preferably applied to networks which are known or predicted to be sparsely connected. By sparsely connected, we mean that the network has at least 50% of potential connections between pairs of nodes which are not present (i.e. the connection coefficients are zero), preferably at least 60% and in some embodiments at least 75%. Indeed, the method of this aspect becomes more efficient as the network becomes sparser, and so can be applied to networks in which 80% or 90% of the potential connections are not present.

This method enables application of Granger-causality in high-dimensional systems (in particular those having 10 or more nodes). Although existing Granger-causality inferences typically work well in low-dimensional systems, the additional steps of the present method in reducing the number of relevant coefficients allows the application of Granger-causality in higher-dimensional systems, particularly (but not exclusively) where these systems are sparsely connected.

The simulations set out below in the detailed description demonstrate in a simulation study that methods according to embodiments of this aspect outperform standard approaches and avoid false positive conclusions about Granger-causality. In comparison with the naive application of Granger-causality inference, these simulations demonstrate the superiority of this method.

Accordingly, the method of this aspect can enable a reliable estimation of Granger-causality. The method of this aspect can be readily applied to various measures for Granger causality and other approaches that are based on vector autoregressive models.

Preferably the step of checking involves calculating the product of the calculated coherence and partial coherence for each combination of nodes and determining whether said product is below said first predetermined threshold. If either of the coherence or the partial coherence is zero, or close to zero, then the resulting product will be zero, or close to zero. This means that, for each coefficient, only a single comparison with the threshold is required.

The first predetermined threshold may be the critical value for partial coherence as defined in Schad et al (2009). Alternatively, the first predetermined threshold may be the critical value for coherence. Alternatively, the first predetermined threshold may be the product of both the critical value for partial coherence and the critical value for coherence.

The second threshold for the estimated connection coefficients may be determined by: separating the estimated coefficients into two groups according to the squared Euclidean distance of the estimated coefficients, a first group containing those coefficients with high values of the coefficients and the second group containing those coefficients with low values; and setting said second threshold as a value which is greater than the value of all coefficients in said second group.

In this manner, the estimated connection coefficients can be separated into two groups and the separation between weak connections and stronger connections, thus permitting a clear distinction to be drawn between the estimated connections which are likely to be entirely due to noise and those which represent a genuine connection. The second threshold may therefore be variably chosen at the appropriate level to separate these two groups. Alternatively, the second threshold may be set in advance.

Preferably the first and second estimating steps for estimating the connection coefficients estimate the autoregressive coefficients of the data set.

Preferably the method further includes the step of screening the data set to remove outliers. As the method of this aspect works on measured data, it may be susceptible to outliers in the data. Outliers are artefacts in the data generally caused by events which are not intended to be measured as part of the recorded data. For example, in EEG data, eye-blinks can cause artefacts of this kind. Removing such outliers from the data set can therefore improve the accuracy of the method.

Preferably the method further includes the step of filtering the data set to remove noise. Again, as the method of this aspect works on measured data, it may be susceptible to noise in those measurements. Accordingly, filtering the data set to remove noise can improve the accuracy of the method.

The screening or filtering can be performed prior to the step of calculating, or could be incorporated into the actual estimation of the coefficients.

In particular embodiments, the network of interacting nodes producing signals are an electroencephalographic (EEG) system. Network structure analysis on EEG data can provide an insight into both brain activity and muscle activity and the resulting networks can be used for comparative purposes, for example against sample networks for particular populations, or as comparators for future studies on the same individual.

The temporal resolution of EEG is in the millisecond range. It is known that brain processing time is of the order of 500 ms and so the method of the present is preferably applied to this data. However, the techniques are equally applicable to other data with lower resolution (e.g. functional magnetic resonance imaging or fRMI which has a temporal resolution of approximately 2 s).

EEG data is currently typically recorded over 20 minute periods. This can lead to practical data collection issues in observing the patient in a constant state (or plurality of states) over such a time period, as well as increasing the probability of artefacts arising. If the time period can be reduced further, perhaps to a few 100 seconds, then these problems can be reduced and/or avoided.

As the method of the present aspect can provide a robust prediction of the network from relatively small quantities of data, the amount of EEG data (and therefore the length of time) needed can potentially be reduced.

The method of the present aspect may include any combination of some, all or none of the above described preferred and optional features.

A second aspect of the present invention provides a method of monitoring brain function in a patient, the method including the steps of: performing an EEG recording on a patient over a period of time; identifying the network connections between the node signals on the EEG using a method according to the above described first aspect, including some, all or none of the optional or preferred features of that aspect.

The methods of the above aspects are preferably implemented by a system according to the third aspect of this invention, as described below, but need not be.

Further aspects of the present invention include computer programs for running on computer systems which carry out the methods of the above aspects, including some, all or none of the preferred and optional features of those aspects.

A third aspect of the present invention provides a system for identifying network connections and estimating connection coefficients between nodes in a data recording of brain activity, the system comprising: a plurality of sensors for recording the brain activity of an individual at different locations over a predetermined period of time to produce a data set; and a processor which is configured to: calculate the coherence and partial coherence between each combination of nodes in the data set; check, for each combination of nodes, if either the coherence or the partial coherence is below a first predetermined threshold and, if so, set the corresponding connection coefficient to zero for all subsequent steps; estimate, from the data set, the connection coefficients for the combinations of nodes for which the connection coefficient has not already been set to zero; for each connection coefficient estimated to be below a second threshold, set said coefficient to zero for all subsequent steps; and re-estimate, from the data set, the connection coefficients for the combinations of nodes for which the connection coefficients have not already been set to zero.

The system of this aspect processes the recorded data and applies two "zeroing" steps prior to the final step of estimating the connection coefficients. These act to remove indirect links (by consideration of partial coherence and coherence). This can reduce or eliminate false positives from the determined network.

The system of this aspect just uses data. It does not rely on any predictions or assumptions about the underlying model.

The system of this aspect assumes a degree of sparseness in the network, implying that some of the coefficients in the adjacency matrix are zero. Based on this assumption the estimation procedure is improved by identifying coefficients which are candidates for zeroing and setting these to zero before performing further calculations or estimations. The method of this aspect is therefore also more efficient at predicting connections in a sparse network than existing methods. Accordingly the method is preferably applied to networks which are known or predicted to be sparsely connected. By sparsely connected, we mean that the network has at least 50% of potential connections between pairs of nodes which are not present (i.e. the connection coefficients are zero), preferably at least 60% and in some embodiments at least 75%. Indeed, the system of this aspect becomes more efficient as the network becomes sparser, and so can be applied to networks in which 80% or 90% of the potential connections are not present.

This processor of this system applies Granger-causality in the high-dimensional system (in particular one having 10 or more nodes). Although existing Granger-causality of data could work well in low-dimensional systems, the processing to reduce the number of relevant coefficients allows the application of Granger-causality in such higher-dimensional systems, particularly (but not exclusively) where these systems are sparsely connected.

Accordingly, the system of this aspect can reliably estimate Granger-causality and can be readily applied to various measures for Granger causality but also to other approaches that are based on vector autoregressive models.

Network structure analysis on brain activity data can provide an insight into both brain activity and muscle activity and the resulting networks can be used for comparative purposes, for example against sample networks for particular populations, or as comparators for future studies on the same individual.

Preferably the processor is configured to calculate the product of the calculated coherence and partial coherence for each combination of nodes and determine whether said product is below said first predetermined threshold. If either of the coherence or the partial coherence is zero, or close to zero, then the resulting product will be zero, or close to zero. This means that, for each coefficient, only a single comparison with the threshold is required.

The first predetermined threshold may be the critical value for partial coherence as defined in Schad et al (2009). Alternatively, the first predetermined threshold may be the critical value for coherence. Alternatively, the first predetermined threshold may be the product of both the critical value for partial coherence and the critical value for coherence.

The processor may be configured to determine said second threshold by: separating the estimated coefficients into two groups according to the squared Euclidean distance of the estimated coefficients, a first group containing those coefficients with high values and the second group containing those coefficients with low values; and setting said second threshold as a value which is greater than the value of all coefficients in said second group.

In this manner, the estimated connection coefficients can be separated into two groups and the separation between weak connections and stronger connections, thus permitting a clear distinction to be drawn between the estimated connections which are likely to be entirely due to noise and those which represent a genuine connection. The second threshold may therefore be variably chosen at the appropriate level to separate these two groups. Alternatively, the second threshold may be set in advance.

Preferably the processor is configured to estimate the connection coefficients by estimating the autoregressive coefficients of the data set.

Preferably the processor is configured to screen the data set to remove outliers. As the processor of this aspect is processing measured brain activity data, it may be susceptible to outliers in the data. Outliers are artefacts in the data generally caused by events which are not intended to be measured as part of the recorded data. For example, in EEG data, eye-blinks in particular can cause artefacts of this kind. Removing such outliers from the data set can therefore improve the accuracy of the system.

Preferably the processor is configured to filter the data set to remove noise. Again, as the processor of this aspect is processing measured brain activity data, it may be susceptible to noise in those measurements. Accordingly, filtering the data set to remove noise can improve the accuracy of the system.

The screening or filtering can be performed prior to the step of calculating, or could be incorporated into the actual estimation of the coefficients.

Preferably the system is applied to electroencephalographic (EEG) data and the plurality of sensors are an electroencephalograph.

The temporal resolution of EEG is in the millisecond range. It is known that brain processing time is of the order of 500 ms and so the method of the present is preferably applied to this data. However, the techniques are equally applicable to other data with lower resolution (e.g. functional magnetic resonance imaging or fRMI which has a temporal resolution of approximately 2 s).

EEG data is currently typically recorded over 20 minute periods. This can lead to practical data collection issues in observing the patient in a constant state (or plurality of states) over such a time period, as well as increasing the probability of artefacts arising. If the time period can be reduced further, perhaps to a few 100 seconds, then these problems can be reduced and/or avoided.

As the system of the present aspect can provide a robust prediction of the network from relatively small quantities of data, the amount of EEG data (and therefore the length of time) needed can potentially be reduced.

The system of the present aspect may include any combination of some, all or none of the above described preferred and optional features.

The system of the present aspect may operate by carrying out a method according to the above first or second aspects of this invention, but need not do so.

BRIEF DESCRIPTION OF THE DRAWINGS

Embodiments of the invention will now be described by way of example with reference to the accompanying drawings in which.

DETAILED DESCRIPTION

Throughout the discussion below, the results are demonstrated for a specific measure for Granger causality, the so-called directed partial correlation (DPC) (Eichler, 2005, 2006).

However, the results apply to any Granger-causality measure that is based on vector autoregressive processes.

Figure 8:
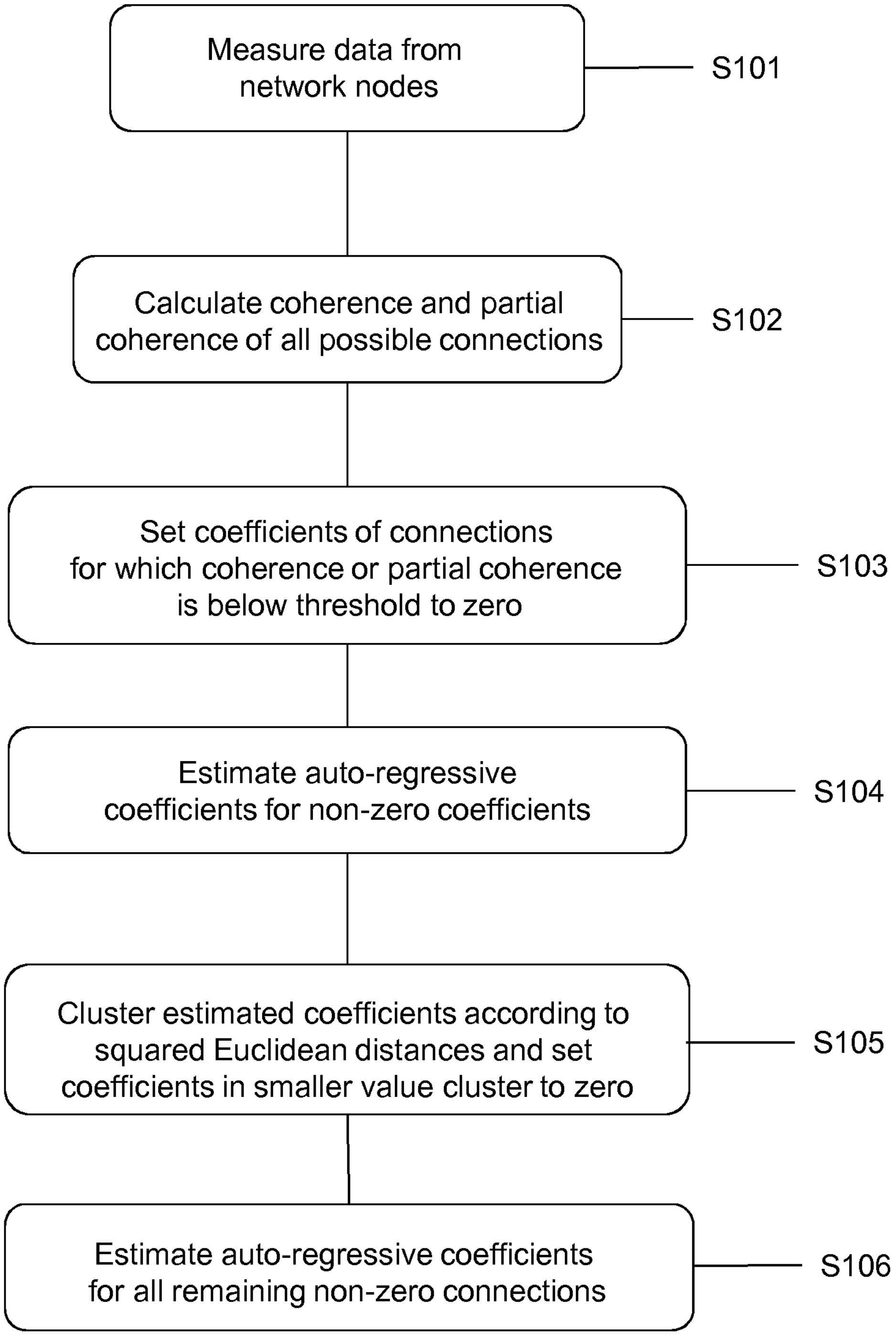
FIG. 8 is a flow chart showing the steps in a method according to an embodiment of the present invention.

A method according to an embodiment of the present invention is shown schematically in the flow chart of FIG. 8. The method involves a three step approach to estimate sparse autoregressive processes. The underlying principle is to rule out some of the coefficients before the actual fitting procedure.

The first analysis step (S102), is to estimate coherence (Priestley, 1981)

$$Coh_{xy}(\omega) = \frac{|CS_{xy}(\omega)|}{\sqrt{S_x(\omega)S_y(\omega)}} \in [0, 1] \quad (3)$$

and partial coherence (Halliday et al., 1995)

$$PC_{xy|x}(\omega) = \frac{|pCS_{xy|x}(\omega)|}{\sqrt{pCS_{x|z}(\omega)pCS_{y|z}(\omega)}} \quad (4)$$

for the processes x and y under investigation according to Schad et al. (2009).

Using a threshold, all coefficients for which the product of coherence and partial coherence is compatible with zero (i.e. falling within a predetermined upper limit, for example are fixed at zero (S103). The product of coherence and partial coherence will be zero if either of them is zero. These coefficients are kept at zero for the reminder of the procedure.

The threshold which is used to determine whether a coefficient is compatible with zero may be the critical value for partial coherence or the critical value for coherence, as defined in Schad et al. (2009).

In the second step (S104) autoregressive coefficients are estimated (Lütkepohl, 2005)

$$\hat{a}_l = \sum_{m=1}^{p} (\hat{R})^{-1}(l, m)\hat{r}(m) \quad (5)$$

with $$\hat{R}(l, m) = \frac{1}{N - p} \sum_{t=p+1}^{N} x(t-l)x(t-m)' \quad (6)$$

and $\hat{r}(m)=\hat{R}(0, m)$. Coefficients with non-significant product of coherence and partial coherence identified in the previous step are kept at zero.

The resulting coefficients are separated into two clusters according to their squared euclidean distance. The coefficients in the cluster with the smaller values are then set to zero (S105). This step accounts for the fact that coherence and partial coherence are symmetric measures and can therefore not rule out single directed connections.

In the third step, autoregressive coefficients are estimated again (Eqs. (5) and (6)—S106). This time all coefficients identified to be compatible with zero in either the first or second step are kept at zero.

The key benefit of this method is that only the non-zero coefficients are estimated in the third step. Since the number of estimated coefficients is dramatically reduced by this procedure, the accuracy of the estimation can be improved. Meaning that less coefficients are estimated from the same number of data points.

The performance of this method can be seen from the simulated data as set out below.

Simulations

Figure 1:
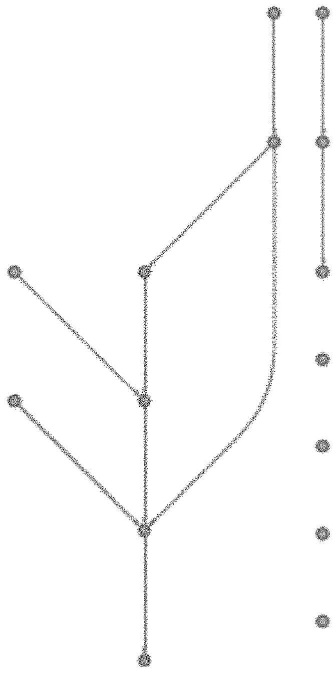
FIG. 1 shows the graph of a simulated 15-dimensional network of coupled white noise processes.
Figure 2:
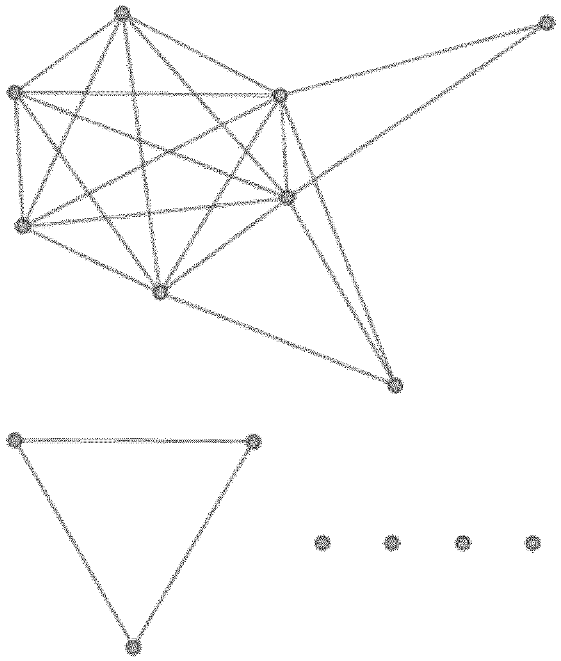
FIGS. 2(*a*) and 2(*b*) show the graphs of the network of FIG. 1 reconstructed using coherence and partial coherence respectively.
Figure 2:
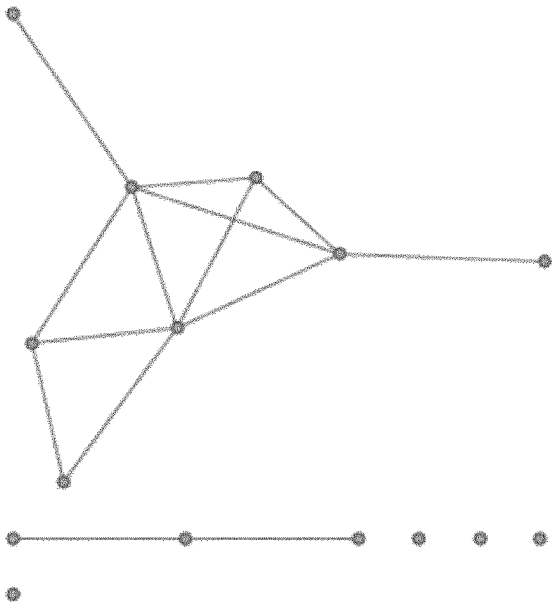
Figure 3:
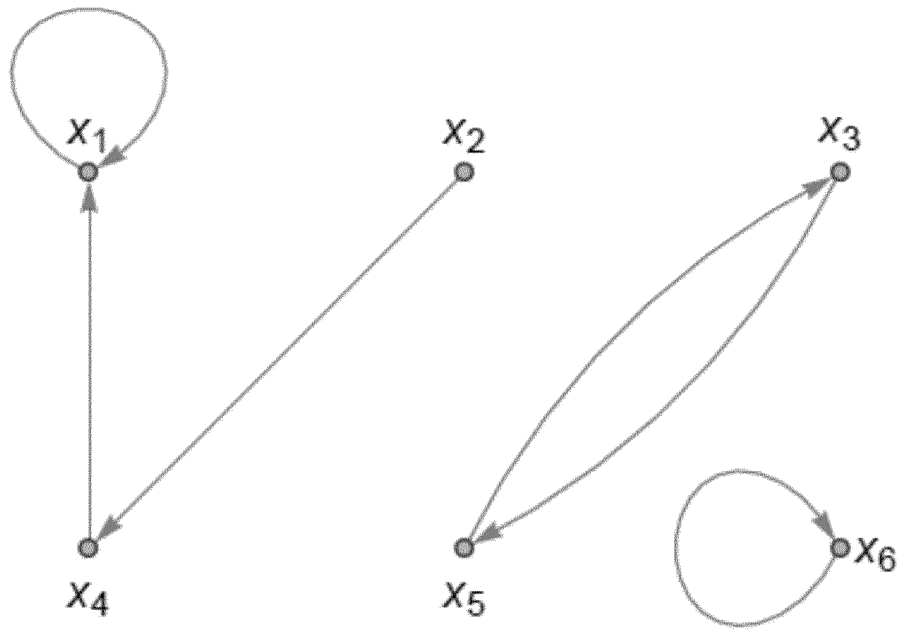
FIG. 3 shows the graph of a simulated six-dimensional autoregressive process of order one.
Figure 5:
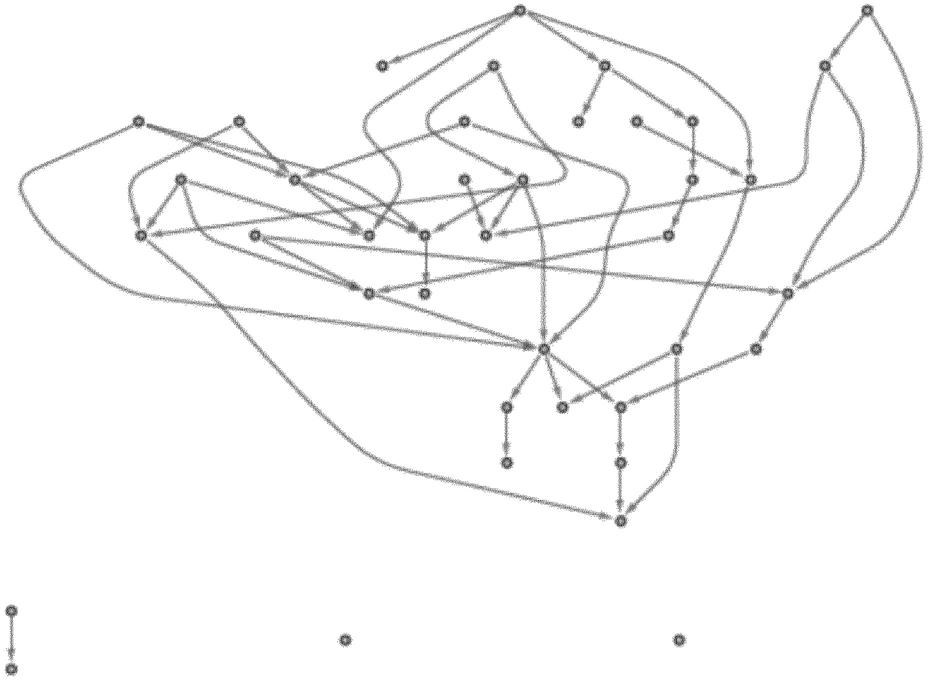
FIG. 5 shows the graph of a simulated 40-dimensional network of coupled white noise processes.
Figure 6:
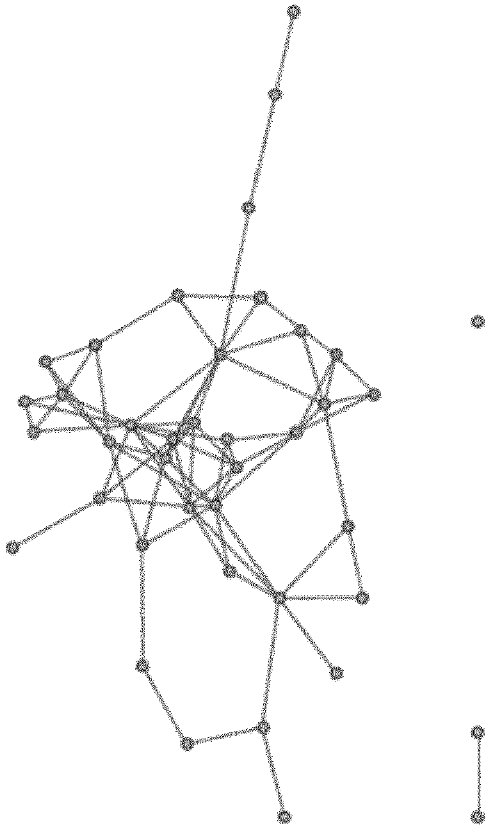
FIGS. 6(*a*) and 6(*b*) show the graphs of the network of FIG. 5 reconstructed using coherence and partial coherence respectively.
Figure 6:
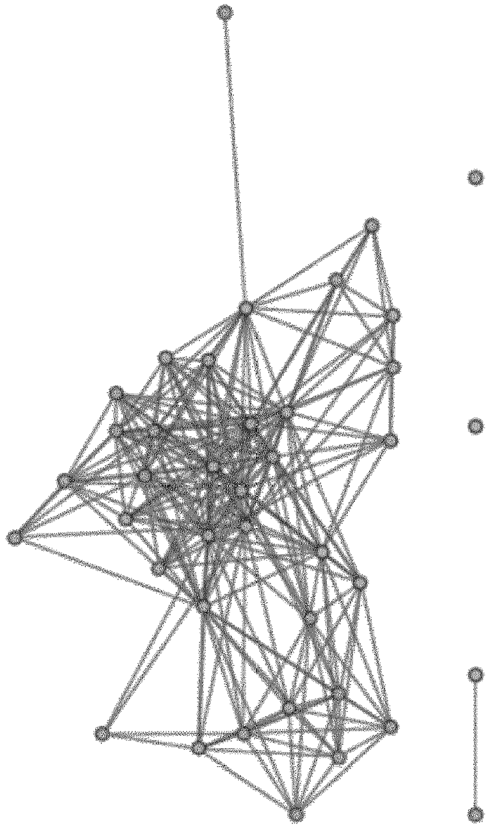
Figure 7:
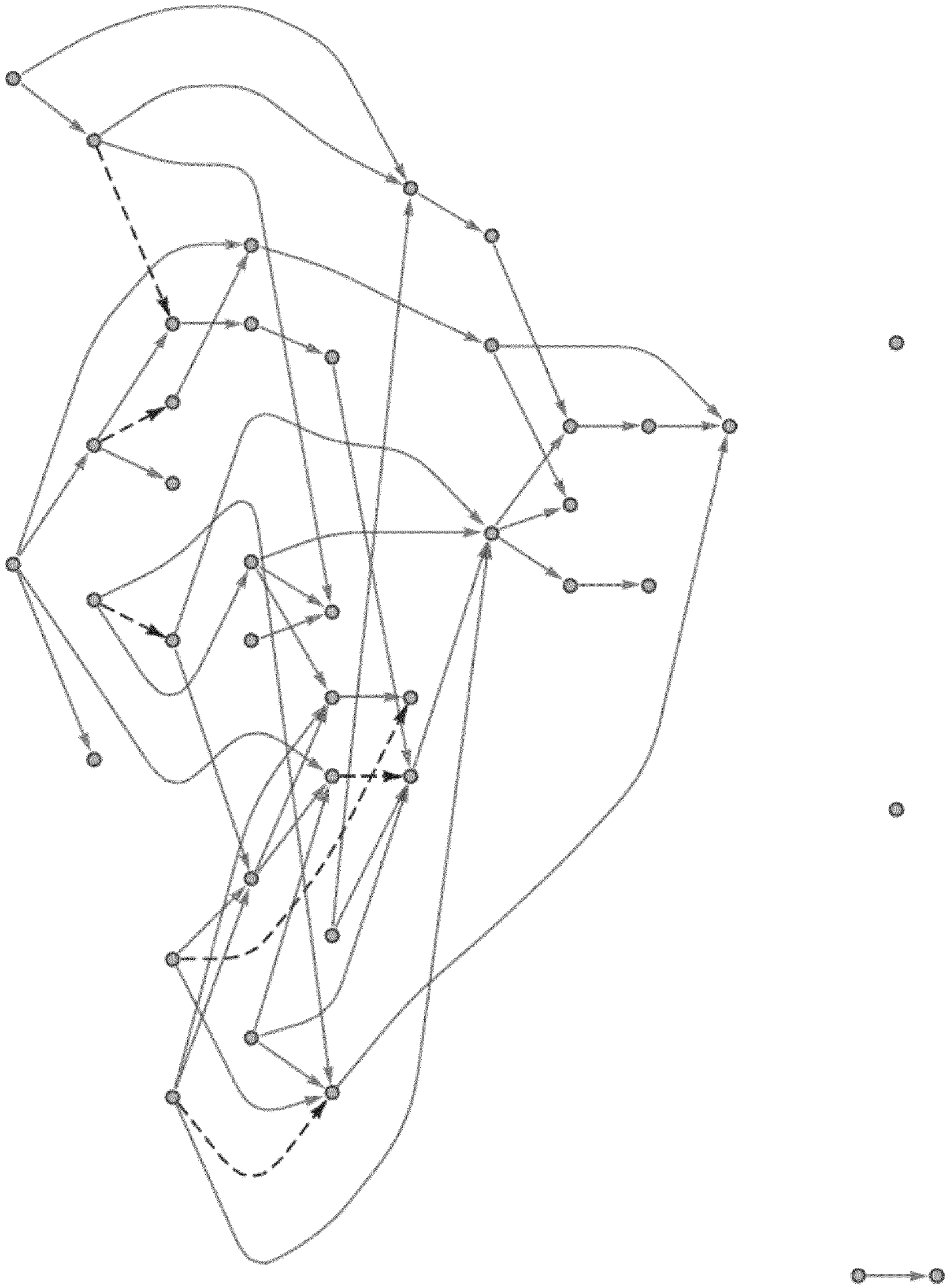
FIG. 7 shows the graph of the reconstruction of the network of FIG. 5 using directed partial correlation analysis with the true process order p=2.
Figure 9:
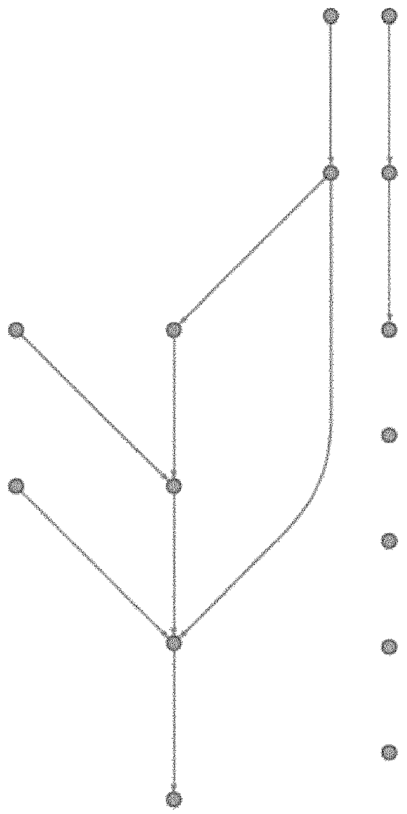
FIGS. 9 and 10 show the networks of the simulation of FIGS. 1 and 5 respectively as estimated using the method of an embodiment of the present invention.
Figure 10:
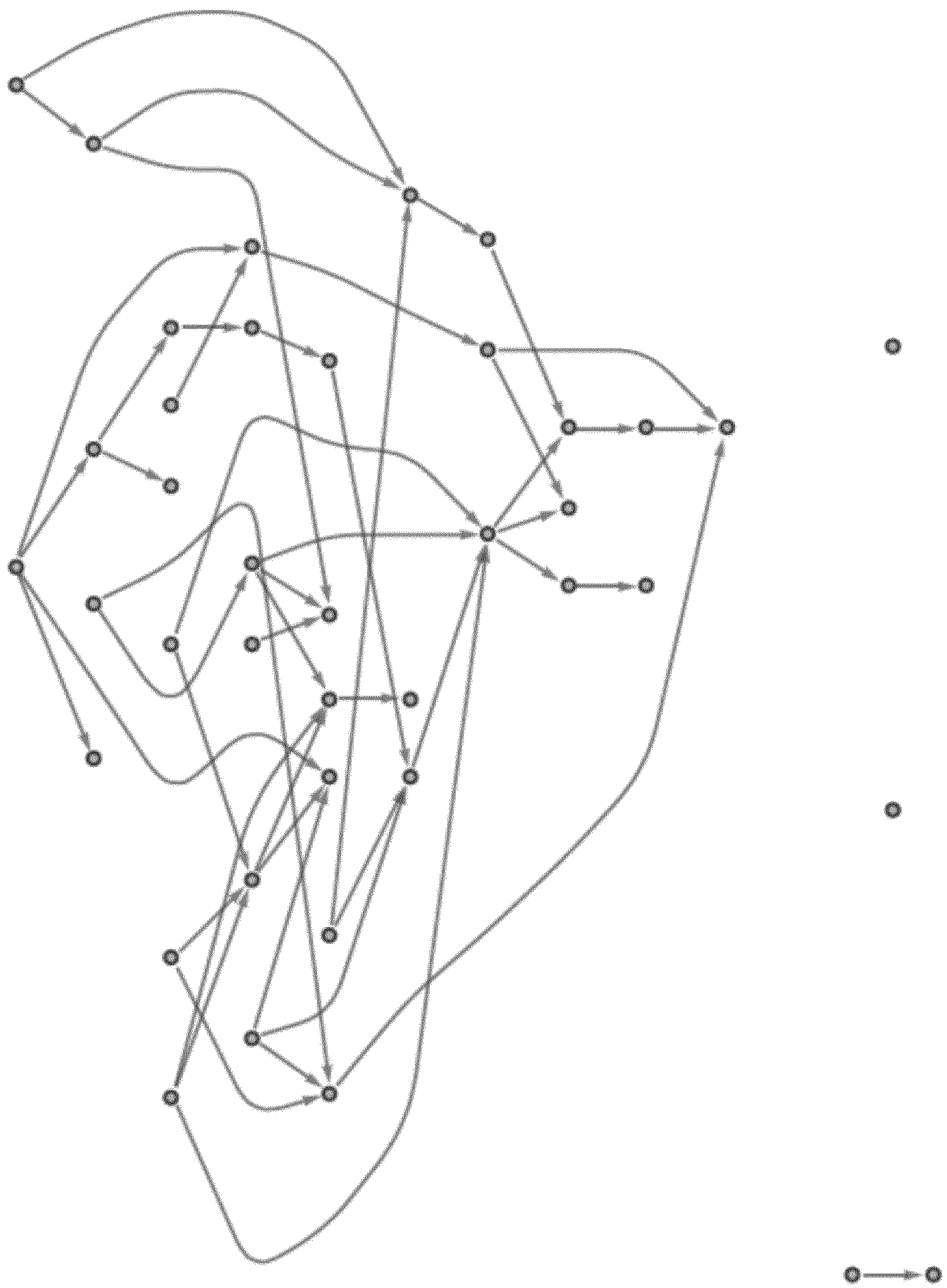

For the 15-dimensional and 40-dimensional networks of coupled white noise processes, which were analysed previously (FIGS. 1 and 5), directed partial correlation was estimated using the method of the embodiment set out above. The resulting graphs are shown in FIGS. 9 and 10, respectively. The true underlying network structure was correctly revealed in both examples.

It should be emphasized that the networks for these simulations were generated randomly. The inventors have tested the method of the above embodiment on over 100 different sparse random networks and all were reconstructed correctly (results not shown).

Figure 4:
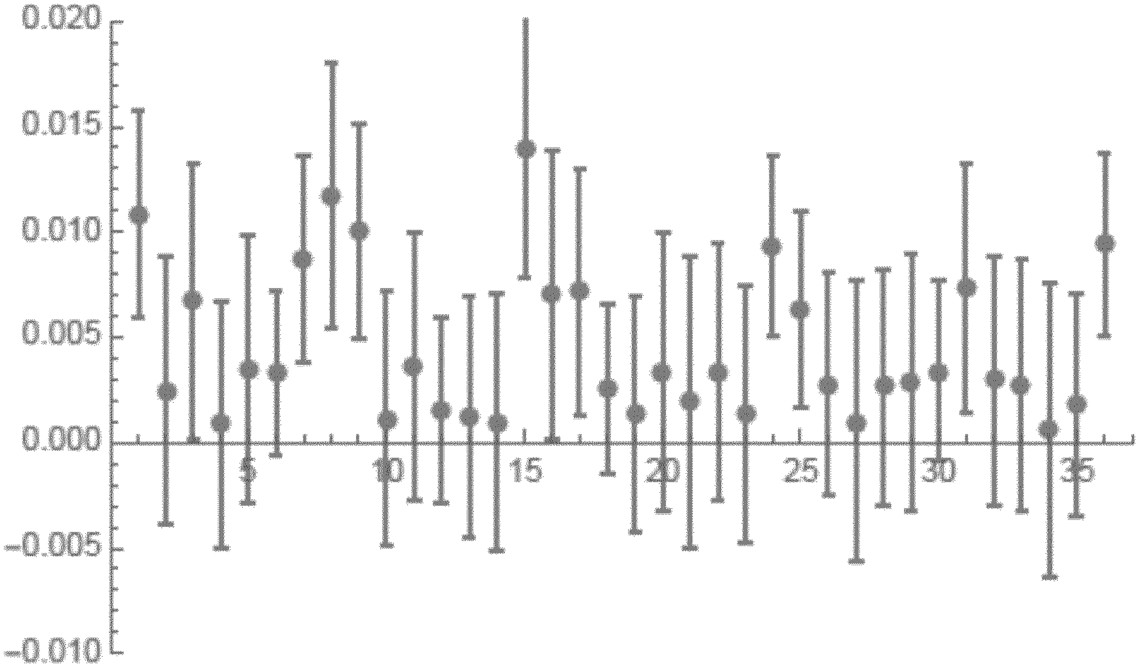
FIG. 4 shows the absolute value of the difference between the true coefficients of the process shown in FIG. 3 and the mean coefficients estimated using the true autoregressive process order p=1.
Figure 11:
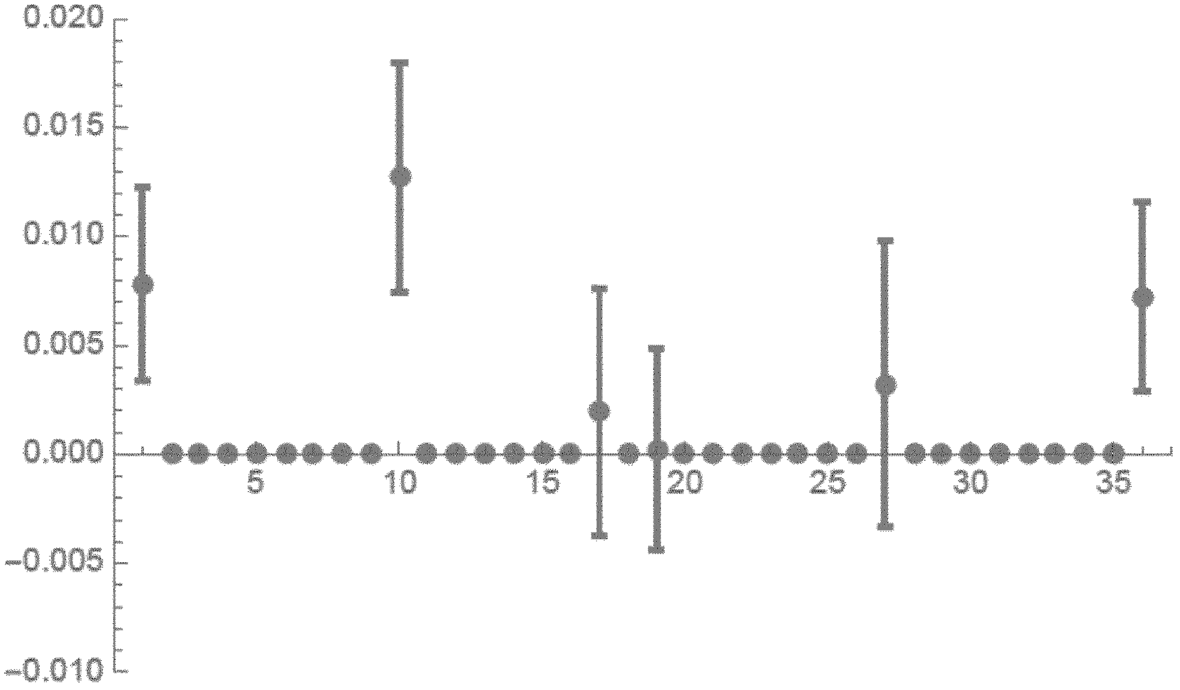
FIG. 11 shows the absolute value of the difference between the true coefficients of the process shown in FIG. 3 and the mean coefficients estimated using a method of an embodiment of the present invention.

The sparse estimation technique also improves estimation of the vector autoregressive coefficients in lower dimensional sparse systems. For example, for the six-dimensional autoregressive process of order one described above (Eqs. (1) and (2)), FIG. 11 is the equivalent to FIG. 4 and shows, for all 36 coefficients, the absolute value of the difference between the true and the mean estimated coefficient using the method according to the above embodiment. Error bars refer to the standard deviation of the mean for 100 realisations. Coefficients that are displayed without error bar are those that were fixed at zero, all of which are truly zero in the simulation. The result shows that the six non-zero coefficients are estimated very close to their respective true value (and closer than in the previously-described process), whilst the 30 coefficients that are zero are all correctly identified as exactly zero.

Figure 12:
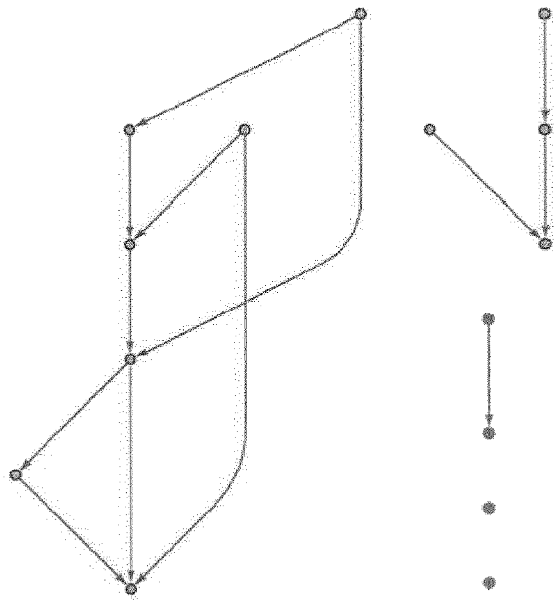
FIG. 12 shows the graph of a simulated 15-dimensional network of coupled white noise processes.
Figure 13:
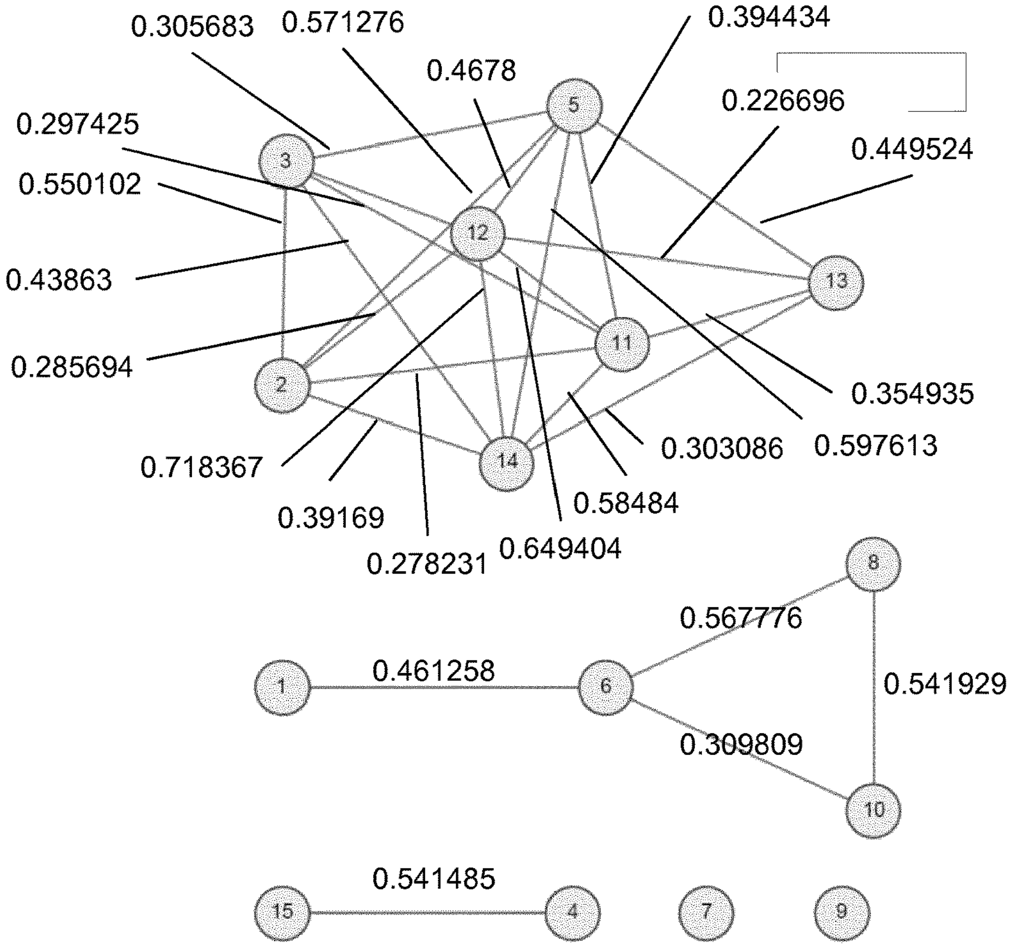
FIG. 13 shows the connections and coefficients of the network of FIG. 12 as predicted using coherence alone.

FIG. 12 shows a further simulated 15-dimensional network of coupled white noise processes. FIG. 13 shows the connections and coefficients of the network of FIG. 12 as predicted using coherence alone. It can be seen that, as well as adding a number of additional connections within the more complex part of the network, this approach also mis-characterises the relationship between nodes 1, 6, 8 and 10.

Figure 14:
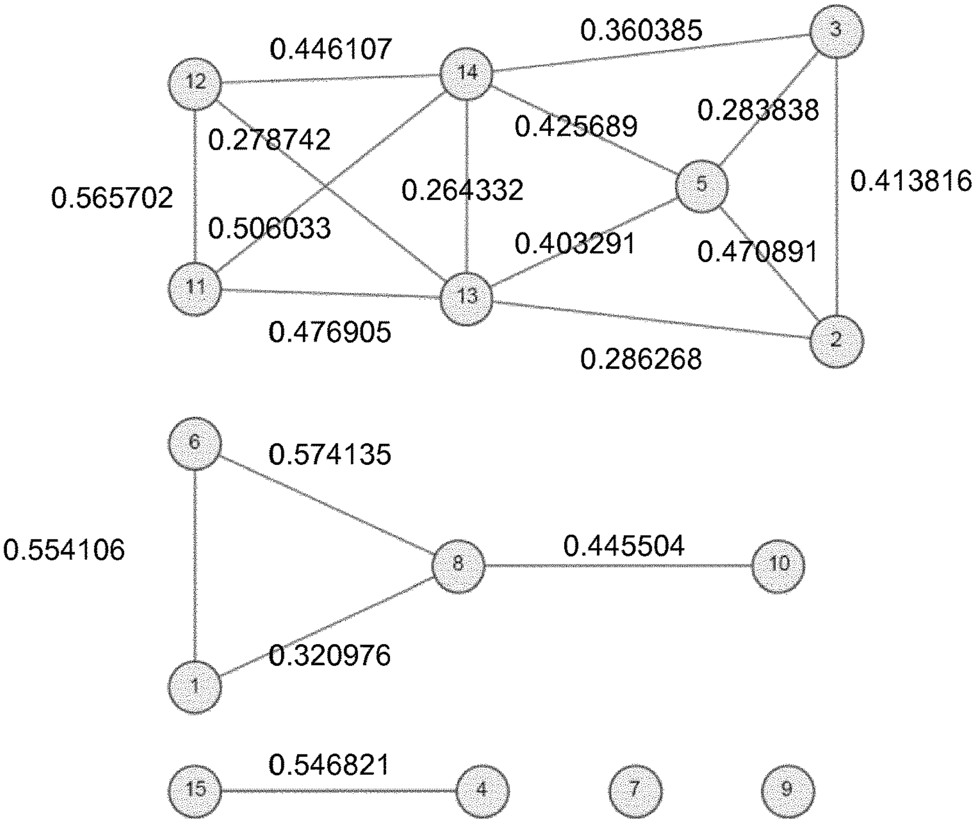
FIG. 14 shows the connections and coefficients of the network of FIG. 12 as predicted using partial-coherence.

FIG. 14 shows the connections and coefficients of the network of FIG. 12 as predicted using partial-coherence. This approach is more successful as it removes a number of indirect links. However, it still incorrectly predicts connections in the more complex part of the network which are not present in the underlying network (false positives) and, like the coherence approach, mis-characterises the relationship between nodes 1, 6, 8 and 10.

Figure 15:
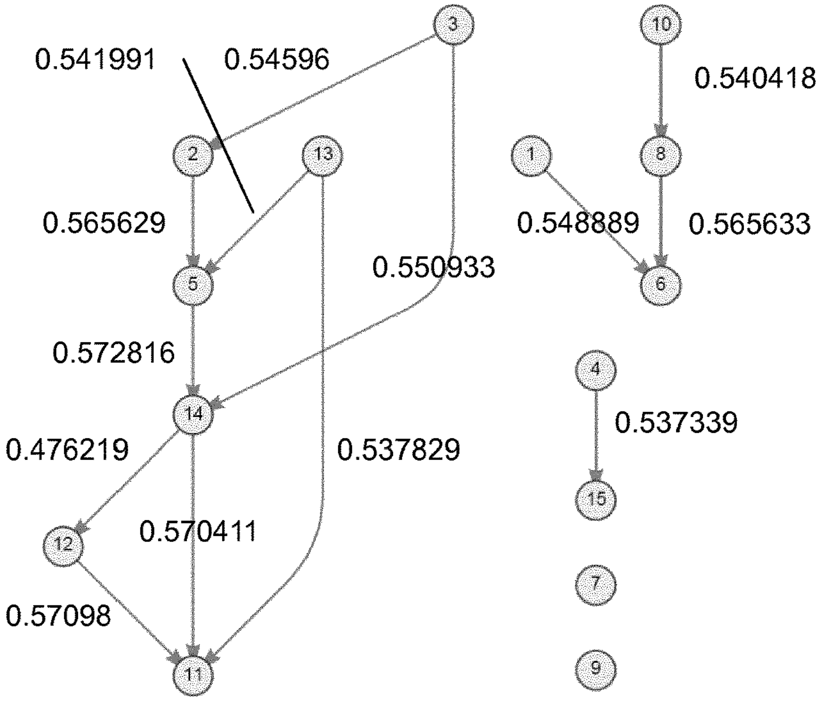
FIG. 15 shows the connections and coefficients of the network of FIG. 12 as calculated using the method of an embodiment of the present invention.

FIG. 15 shows the connections and coefficients of the network of FIG. 12 as calculated using the method of the embodiment described above. It can be seen from a comparison with FIG. 12 that the network is completely accurately mapped.

Figure 16:
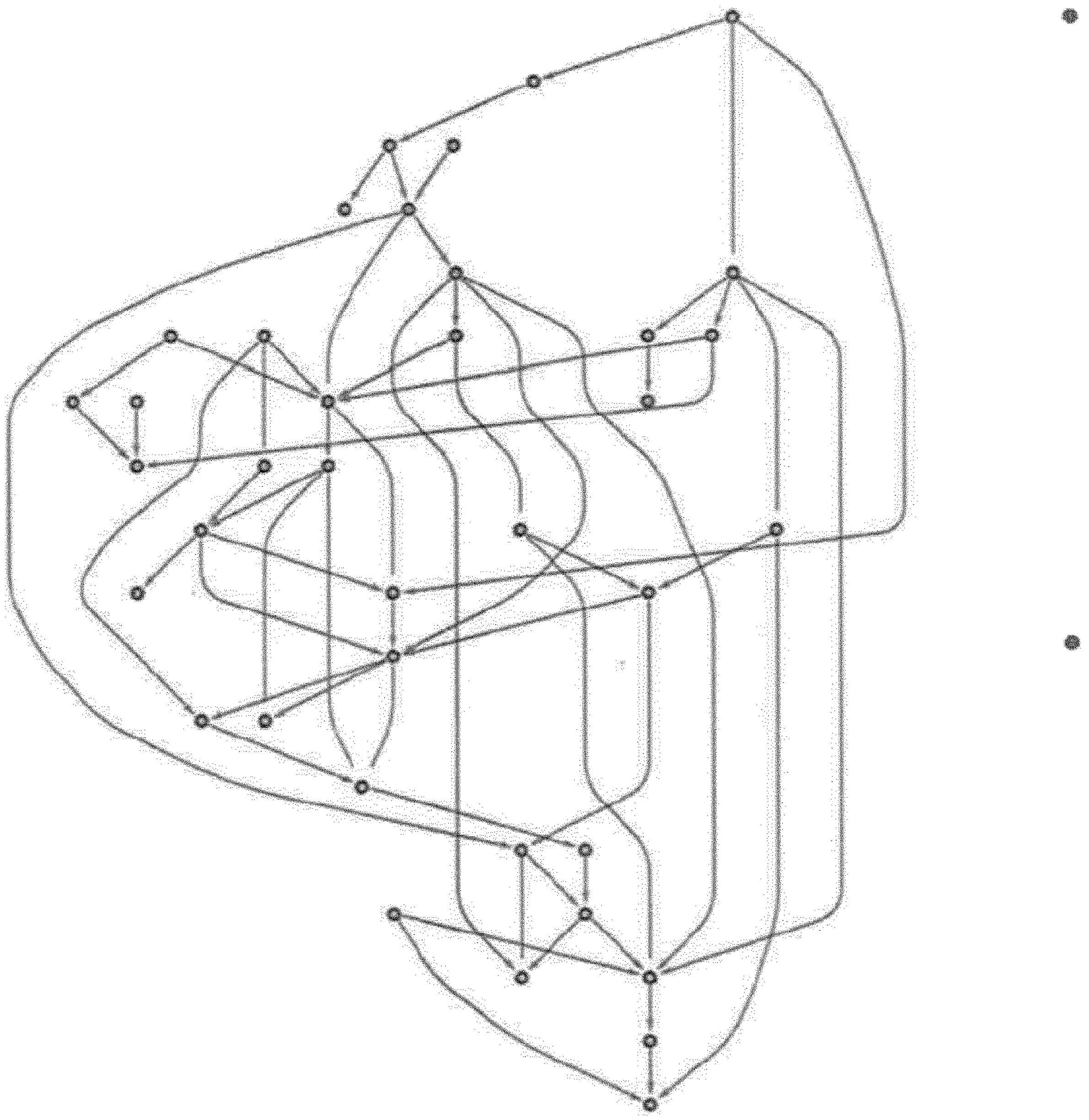
FIG. 16 shows the graph of a simulated 40-dimensional network of coupled white noise processes.
Figure 17:
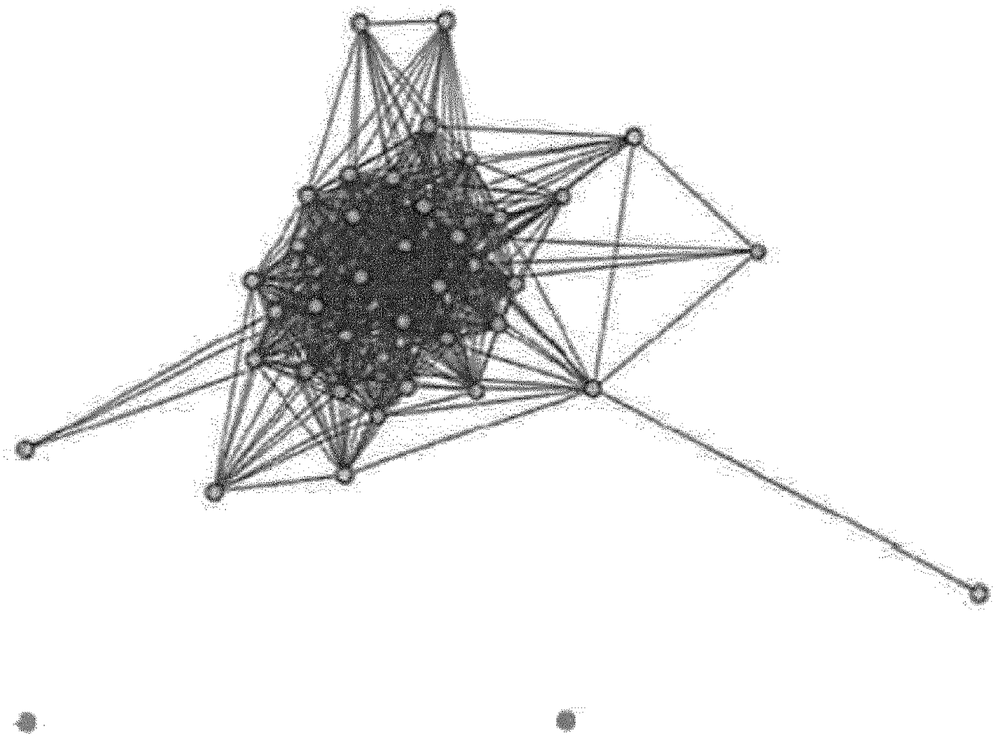
FIG. 17 shows the predicted network of FIG. 16 reconstructed using coherence alone.
Figure 18:
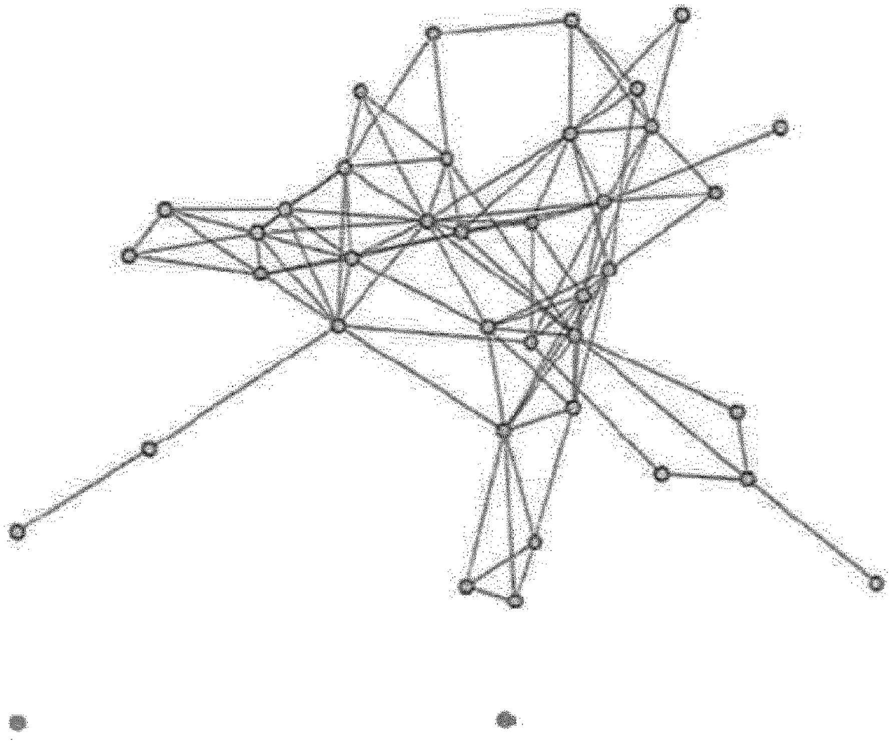
FIG. 18 shows the predicted network of FIG. 16 reconstructed using partial coherence.

FIG. 16 shows a further simulated 40-dimensional network of coupled white noise processes. FIG. 17 shows the predicted network using coherence, and it can be seen that as the dimension of the network increases, the number of false positives generated in this approach can completely overwhelm the true connections. FIG. 18 shows the predicted network using partial coherence. As with the previous simulation, this cuts out a significant number of false positive connections, but still does not completely reproduce the underlying network. The method of the embodiment described above accurately reproduces the network shown in FIG. 16.

Example Application

Figure 19:
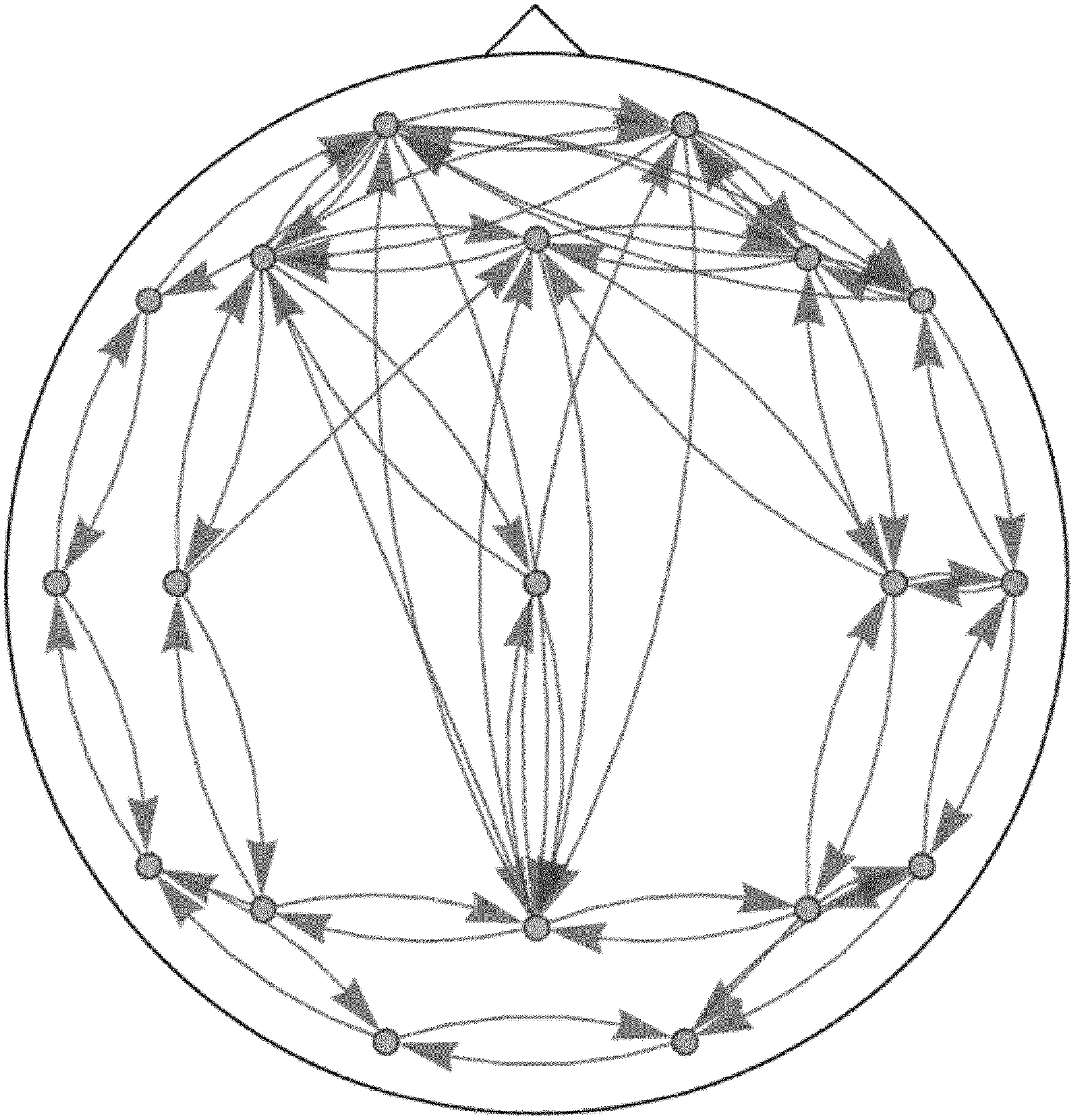
FIG. 19 shows the interaction structure of electroencephalogram (EEG) data from a healthy volunteer.

In an exemplary application, electroencephalogram (EEG) data of one healthy volunteer is analysed. EEG recordings were obtained during eyes closed. The signal was sampled at 512 Hz. Twenty electrodes were placed on the scalp according to the 10-20 system. Data were down-sampled to 200 Hz and a model order of p=2 was used in the sparse estimation. One segment of 100 s was analysed. The interaction structure that was revealed is shown in FIG. 19. As expected in a healthy individual, there are a wide range of interconnections between the various parts of the brain.

Figure 20:
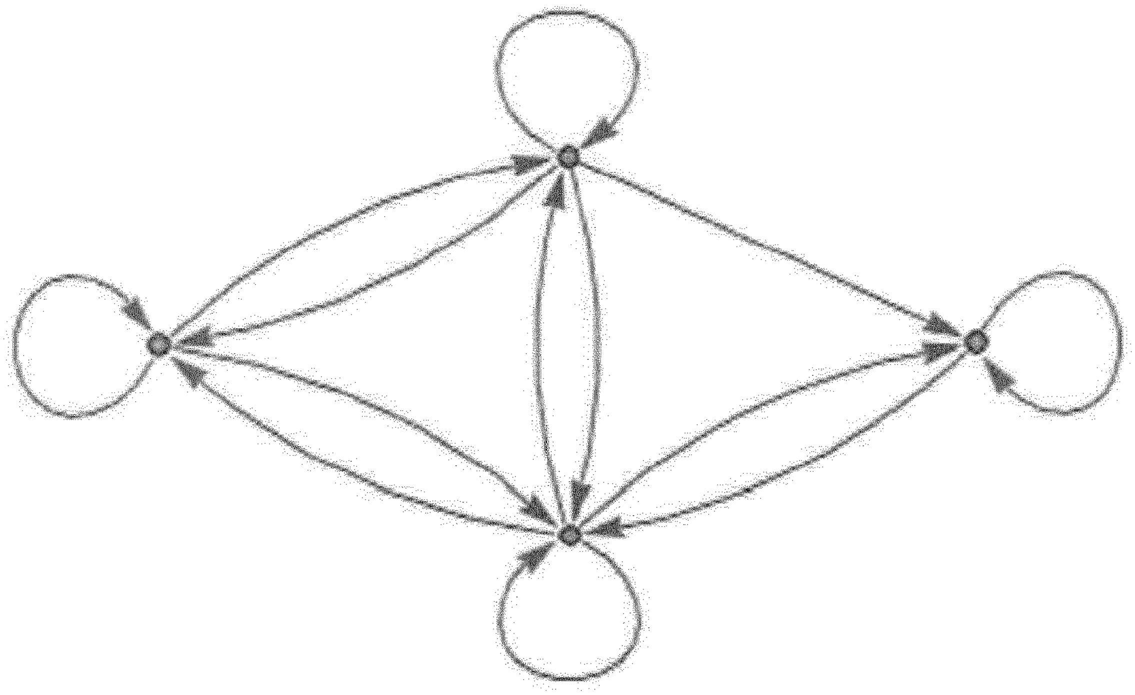
FIG. 20 illustrates, schematically, the kind of network that would be expected in the brain of a healthy individual.
Figure 21:
FIG. 21 illustrates, schematically, the kind of network that would be expected in the brain of an individual with mild cognitive impairment.

FIGS. 20 and 21 illustrate, schematically, the kinds of networks that would be expected for a healthy individual and an individual with mild cognitive impairment. The nodes have been simplified to the frontal, central, temporary and occipital regions (4 channel EEG). As can be seen in FIG. 20, a healthy individual would be expected to have interconnections between all of the regions and within each individual region (as the nodes are effectively identical, they have not been labelled in FIG. 20).

FIG. 21 shows that, in an individual with mild cognitive impairment, whilst there is connection within each region, the interconnection between each region is significantly reduced, and generally only involves flow in one direction from frontal to occipital with little or no return flow from the occipital or temporal regions, and no connections between non-adjacent regions.

Although 4 channel EEG does not produce the high-dimensional data discussed previously, analysis of the data from such EEG monitoring may be particularly useful as 4 channel EEG devices are available which can be readily used in the primary care setting and by individuals themselves.

Further Developments

The sparse estimation technique of the present invention can readily be applied to frequency-domain measures for Granger-causality such as re-normalised partial directed coherence (Schelter et al., 2009). This will allow investigating networks at different frequencies which is of particular interest in EEG analysis.

It should be emphasised that the method of the embodiments set out above is data driven. This means that the sparse coefficient matrix is estimated based on a given data set measured from the nodes. Zeros are placed according to coherence and partial coherence estimated from the data set. Should the underlying network not be sparse, the algorithm will simply proceed to estimate all coefficients in the way that the underlying estimation procedure does.

However, measurements are never exact and observational noise can impact Granger causality inference (Sommerlade et al., 2015). In order to deal with observational noise, the sparse estimation technique presented here can be combined with the state space model approach presented in Sommerlade et al. (2015).

In addition to observational noise, measured data can be afflicted by outliers. For example, for EEG data these outliers include eye-blink artefacts. When estimating autoregressive processes, outliers such as eye-blinks can be removed using weighted robust Kalman filtering (Ting et al., 2007) or the more general outlier robust Kalman filtering (Agamennoni et al., 2011). The methods described herein can be combined with these approaches to further improve the estimation technique.

Further Uses

Methods of predicting according to embodiments of this invention can be used in a variety of settings. As shown above, they have particular use in the analysis of EEG data and, from the predicted networks, it is possible to carry out further assessments or make determinations of the cognitive function of the individual from whom the data is taken.

The network prediction methods can be used in a variety of ways. In addition to diagnosis (for example by comparison of the network obtained from EEG data from an individual against comparative networks for healthy individuals and those with cognitive impairments), the network predictions can be used to monitor the response of an individual to treatment for cognitive impairment. For example, a record of the networks derived from EEG data from an individual undergoing treatment can be maintained and changes monitored over time. An effective treatment may either slow or stop the deterioration in the individual's cognitive function (as represented by the number and/or strength of connections in the network), or may result in a reversal of previous decline (as represented by an increase in the number and/or strength of connections in the network).

The network prediction methods can also be used as a discriminator to identify or screen candidates for trials of a particular treatment by allowing identification of individuals with particular characteristics of cognitive function at the neural level. The network prediction methods can also be used to screen to ensure either that all participants in the trial have the same, or similar, cognitive impairments, or that participants having a wide range of cognitive impairments are selected.

The network prediction methods can also be used in conjunction with targeted response questions to test specific responses and determine whether this affects the pattern of responses within the brain during that testing.

General Provisions

The systems and methods of the above embodiments may be implemented in whole or in part in a computer system (in particular in computer hardware or in computer software) in addition to the structural components and user interactions described.

The term "computer system" includes the hardware, software and data storage devices for embodying a system or carrying out a method according to the above described embodiments. For example, a computer system may comprise a central processing unit (CPU), input means, output means and data storage. Preferably the computer system has a monitor to provide a visual output display. The data storage may comprise RAM, disk drives or other computer readable media. The computer system may include a plurality of computing devices connected by a network and able to communicate with each other over that network.

The methods of the above embodiments may be provided as computer programs or as computer program products or computer readable media carrying a computer program which is arranged, when run on a computer, to perform the method(s) described above.

The term "computer readable media" includes, without limitation, any non-transitory medium or media which can be read and accessed directly by a computer or computer system. The media can include, but are not limited to, magnetic storage media such as floppy discs, hard disc storage media and magnetic tape; optical storage media such as optical discs or CD-ROMs; electrical storage media such as memory, including RAM, ROM and flash memory; and hybrids and combinations of the above such as magnetic/optical storage media.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

REFERENCES

Agamennoni, G., Nieto, J., Nebot, E., May 2011. An outlier-robust kalman filter. In: Robotics and Automation (ICRA), 2011 IEEE International Conference on. pp. 1551-1558.

Arnhold, J., Grassberger, P., Lehnertz, K., Elger, C. E., 1999. A robust method for detecting interdependencies: Application to intracranially recorded EEGs. Physica D 134, 419-430.

Arnold, M., Miltner, W. H. R., Witte, H., Bauer, R., Braun, C., 1998. Adaptive AR modeling of nonstationary time series by means of Kalman filtering. IEEE T. Bio-Med. Eng. 45, 553-562.

Baccalá, L. A., Sameshima, K., 2001. Partial directed coherence: A new concept in neural structure determination. Biol. Cybern. 84, 463-474.

Bahraminasab, A., Ghasemi, F., Stefanovska, A., McClintock, P. V. E., Friedrich, R., 2009. Physics of brain dynamics: Fokker-Planck analysis reveals changes in EEG delta and theta activity during anaesthesia. New J. Phys. 11, 103051.

Bowers, E. J., Murray, A., 2004. Interaction between cardiac beat-to-beat interval changes and systolic blood pressure changes. Clin. Autonom. Res. 14, 92-98.

Chen, W. Y., Wasterlain, C. G., 2006. Status epilepticus: Pathophysiology and management in adults. Lancet Neurol. 5, 246-256.

Chicharro, D., Andrzejak, R. G., 2009. Reliable detection of directional couplings using rank statistics. Phys. Rev. E 80, 026217.

Dahlhaus, R., 2000. Graphical interaction models for multivariate time series. Metrika 51, 157-172.

Dahlhaus, R., Eichler, M., 2003. Causality and graphical models for time series. In: Green, P., Hjort, N., Richardson, S. (Eds.), Highly Structured Stochastic Systems. Oxford University Press, pp. 115-137.

Dhamala, M., Rangarajan, G., Ding, M., 2008. Estimating Granger causality from Fourier and wavelet transforms of time series data. Phys. Rev. Lett. 100, 018701.

Eichler, M., 2000. Markov properties for graphical time series models. Preprint University of Heidelberg.

Eichler, M., May 2005. A graphical approach for evaluating effective connectivity in neural systems. Philos Trans R Soc Lond B Biol Sci 360 (1457), 953-967.

Eichler, M., 2006. Graphical modeling of dynamic relationships in multivariate time series. In: Schelter, B., Winterhalder, M., Timmer, J. (Eds.), Handbook of Time Series Analysis. Wiley-VCH, Ch. 14, pp. 335-372.

Frenzel, S., Pompe, B., 2007. Partial mutual information for coupling analysis of multivariate time series. Phys. Rev. Lett. 99, 204101.

Geweke, J., 1982. Measurement of linear dependence and feedback between multiple time series. J. Am. Stat. Assoc. 77, 304-313.

Geweke, J., 1984. Measures of conditional linear dependence and feedback between time series. J. Am. Stat. Assoc. 79, 907-915.

Granger, J., 1969. Investigating causal relations by econometric models and cross-spectral methods. Econometrica 37, 424-438.

Halliday, D. M., Rosenberg, J. R., 2000. On the application and estimation and interpretation of coherence and pooled coherence. J. Neurosci. Meth. 100, 173-174.

Halliday, D. M., Rosenberg, J. R., Amjad, A. M., Breeze, P., Conway, B. A., Farmer, S. F., 1995. A framework for the analysis of mixed time series/point process data—Theory and application to the study of physiological tremor, single motor unit discharges and electromyograms. Prog. Biophys. molec. Biol. 64, 237-278.

Hesse, W., Möller, E., Arnold, M., Schack, B., 2003. The use of time-variant EEG Granger causality for inspecting directed interdependencies of neural assemblies. J. Neurosci. Meth. 124, 27-44.

Kamiński, M. J., Blinowska, K. J., 1991. A new method of the description of the information flow in the brain structures. Biol. Cybern. 65, 203-210.

Kamiński, M. J., Blinowska, K. J., Szelenberger, W., 1997. Topographic analysis of coherence and propagation of EEG activity during sleep and wakefulness. Electroenceph. Clin. Neurophys. 102, 216-227.

Keyl, C., Dambacher, M., Schneider, A., Passino, C., Wegenhorst, U., Bernardi, L., 2000. Cardiocirculatory coupling during sinusoidal baroreceptor stimulation and fixed-frequency breathing. Clinical Science 99, 113-124.

Korzeniewska, A., Kasicki, S., Kamiński, M. J., Blinowska, K. J., 1997. Information flow between hippocampus and related structures during various types of rat's behavior. J. Neurosci. Meth. 73, 49-60.

Lee, H., Lee, D. S., Kand, H., Kim, B.-N., Chung, K., 2011. Sparse brain network recovery under compressed sensing. IEEE T. Med. Imaging 30, 1154-1165.

Lütkepohl, H., 2005. New Introduction to Multiple Time Series Analysis. Springer, pp. 82-87.

Nollo, G., Faes, L., Porta, A., Antolini, R., Ravelli, F., 2005. Exploring directionality in spontaneous heart period and systolic pressure variability interactions in humans: Implications in the evaluation of baroreflex gain. Am. J. Physiol. Heart. Circ. Physiol. 288, 1777-1785.

Nolte, G., Ziehe, A., Nikulin, V. V., Schl ogl, A., Kr amer, N., Brismar, T., Müller, K.-R., 2008. Robustly estimating the flow direction of information in complex physical systems. Phys. Rev. Lett. 100, 234101.

Paluš, M., Stefanovska, A., 2003. Direction of coupling from phases of interacting oscillators: An information-theoretic approach. Phys. Rev. E 67, 055201(R).

Paluš, M., Vejmelka, M., 2007. Directionality of coupling from bivariate time series: How to avoid false causalities and missed connections. Phys. Rev. E 75, 056211.

Pitzalis, M. V., Mastropasqua, F., Massari, F., Passantino, A., Colombo, R., Mannarini, A., Forleo, C., Rizzon, P., 1998. Effect of respiratory rate on the relationships between RR interval and systolic blood pressure fluctuations: A frequency-dependent phenomenon. Cardiovasc. Res. 38, 332-339.

Pompe, B., Blidh, P., Hoyer, D., Eiselt, M., 1998. Using mutual information to measure coupling in the cardiorespiratory system. IEEE Eng. Med. Biol. Mag. 17, 32-39.

Priestley, M. B., 1981. Spectral Analysis and Time Series. Academic Press, London, pp 655-668.

Prusseit, J., Lehnertz, K., 2008. Measuring interdependences in dissipative dynamical systems with estimated Fokker-Planck coefficients. Phys. Rev. E 77, 041914.

Romano, M. C., Thiel, M., Kurths, J., Grebogi, C., 2007. Estimation of the direction of the coupling by conditional probabilities of recurrence. Phys. Rev. E 76, 036211.

Rosenblum, M. G., Cimponeriu, L., Bezerianos, A., Patzak, A., Mrowka, R., 2002. Identification of coupling direction: Application to cardiorespiratory interaction. Phys. Rev. E 65, 041909.

Rosenblum, M. G., Pikovsky, A. S., 2001. Detecting direction of coupling in interacting oscillators. Phys. Rev. E 64, 045202(R).

Sameshima, K., Baccalá, L. A., 1999. Using partial directed coherence to describe neuronal ensemble interactions. J. Neurosci. Meth. 94, 93-103.

Schad, A., Nawrath, J., Jachan, M., Henschel, K., Spindeler, L., Timmer, J., Schelter, B., 2009. Approaches to the detection of direct directed interactions in neuronal networks. In: Velazquez, J. L. P., Wennberg, R. (Eds.), Coordinated Activity in the Brain. Springer, Ch. 3, pp. 43-64.

Schelter, B., Timmer, J., Eichler, M., 2009. Assessing the strength of directed influences among neural signals using renormalized partial directed coherence. J. Neurosci. Meth. 179, 121-130.

Schreiber, T., 2000. Measuring information transfer. Phys. Rev. Lett. 85, 461-464.

Sommerlade, L., Thiel, M., Mader, M., Mader, W., Timmer, J., Platt, B., Schelter, B., January 2015. Assessing the strength of directed influences among neural signals: an approach to noisy data. J Neurosci Methods 239, 47-64.

Staniek, M., Lehnertz, K., 2008. Symbolic transfer entropy. Phys. Rev. Lett. 100, 158101.

Strogatz, S. H., March 2001. Exploring complex networks. Nature 410 (6825), 268-276.

Tass, P., Rosenblum, M. G., Weule, J., Kurths, J., Pikovsky, A. S., Volkmann, J., Schnitzler, A., Freund, H. J., 1998. Detection of n: m phase locking from noisy data: Application to magnetoencephalography. Phys. Rev. Lett. 81, 3291-3295.

Ting, J.-A., Theodorou, E., Schaal, S., October 2007. A Kalman filter for robust outlier detection. In: Intelligent Robots and Systems, 2007. IROS 2007. IEEE/RSJ International Conference on. pp. 1514-1519.

Vejmelka, M., Paluš, M., 2008. Inferring the directionality of coupling with conditional mutual information. Phys. Rev. E 77, 026214.

All references referred to above are hereby incorporated by reference.

The invention claimed is:

1. A method of monitoring brain function in a patient using a plurality of electroencephalography (EEG) sensors, the method including:

recording a plurality of EEG signals using the plurality EEG sensors over a period of time to form a data set of EEG signals;

determining a network of relationships among the EEG signals in the data set, the network comprising a plurality of nodes corresponding to the plurality of EEG sensors, using a processor, the determining comprising:

calculating coherence and partial coherence for pairs of nodes in the network, wherein calculating the coherence and partial coherence for a first pair of nodes in the network comprises calculating the coherence and partial coherence between EEG signals recorded by a pair of EEG sensors corresponding to the first pair of nodes;

setting, for each of multiple pairs of nodes in the network, a connection coefficient for the pair of nodes to zero using the coherence and partial coherence calculated for the pair of nodes and a first threshold;

after the setting, estimating, using the EEG signals in the data set, connection coefficients for pairs of nodes for which respective connection coefficients have not already been set to zero to obtain a first set of connection coefficients;

setting any connection coefficients in the first set of connection coefficients below a second threshold to zero; and estimating, using the EEG signals in the data set, connection coefficients for pairs of nodes for which respective connection coefficients have not already been set to zero to obtain a second set of connection coefficients; and monitoring brain function in the patient using the determined network of relationships.

2. The method of claim 1, wherein setting, for each of multiple pairs of nodes in the network, a connection coefficient for the pair of nodes to zero using the coherence and partial coherence calculated for the pair of nodes and a first threshold comprises:

determining, for a first pair of the multiple pairs of nodes, whether each of the coherence and partial coherence for the first pair nodes is below the first threshold.

3. The method of claim 1, wherein estimating the connection coefficients for pairs of nodes for which respective connection coefficients have not already been set to zero to obtain a first set of connection coefficients comprises estimating autoregressive coefficients.

4. The method of claim 1, wherein the network of relationships is known or predicted to be sparsely connected.

5. The method of claim 1, further including:

screening the data set to remove outliers.

6. The method of claim 1, further including:

filtering the data set to remove noise.

7. The method of claim 1, wherein the plurality of EEG sensors includes 4 EEG sensors.

8. The method of claim 1, wherein the plurality of EEG sensors includes 20 EEG sensors.

9. The method of claim 1, wherein the data set of EEG signals includes an EEG signal comprising 20,000 points.

10. The method of claim 1, wherein monitoring brain function in the patient using the determined network of relationships comprises:

comparing the determined network of relationships to another network of relationships determined for the patient.

11. The method of claim 1, wherein monitoring brain function in the patient using the determined network of relationships comprises:

determining a second network of relationships among EEG signals in a second plurality of EEG signals recorded for the patient; and comparing the determined network of relationships to the second network of relationships.

12. The method of claim 1, wherein monitoring brain function in the patient using the determined network of relationships comprises:

comparing the determined network of relationships to another network of relationships determined for another patient.

13. The method of claim 1, wherein estimating connection coefficients for pairs of nodes for which respective connection coefficients have not already been set to zero to obtain a second set of connection coefficients comprises estimating autoregressive coefficients.

* * * * *